US011395906B2

(12) United States Patent
Palushi et al.

(10) Patent No.: US 11,395,906 B2
(45) Date of Patent: Jul. 26, 2022

(54) COMBINED SINUPLASTY AND SEEKER INSTRUMENT WITH NAVIGATION AND ILLUMINATION MODALITIES

(71) Applicant: Acclarent, Inc., Irvine, CA (US)

(72) Inventors: Jetmir Palushi, Irvine, CA (US); Fatemeh Akbarian, Rancho Palos Verdes, CA (US); Athanasios Papadakis, Newport Beach, CA (US); Henry F. Salazar, Pico Rivera, CA (US); Jordan R. Trott, Redondo Beach, CA (US)

(73) Assignee: Acclarent, Inc., Irvine, CA (US)

( * ) Notice: Subject to any disclaimer, the term of this patent is extended or adjusted under 35 U.S.C. 154(b) by 221 days.

(21) Appl. No.: 16/666,488

(22) Filed: Oct. 29, 2019

(65) Prior Publication Data
US 2020/0188640 A1    Jun. 18, 2020

Related U.S. Application Data

(60) Provisional application No. 62/778,376, filed on Dec. 12, 2018.

(51) Int. Cl.
*A61B 1/233* (2006.01)
*A61M 25/10* (2013.01)
(Continued)

(52) U.S. Cl.
CPC ............. *A61M 25/10* (2013.01); *A61B 34/20* (2016.02); *A61B 1/06* (2013.01); *A61B 1/233* (2013.01);
(Continued)

(58) Field of Classification Search
CPC .......... A61B 1/233; A61B 2017/00367; A61B 90/30; A61M 2025/09116;
(Continued)

(56) References Cited

U.S. PATENT DOCUMENTS

| 7,720,521 B2 | 5/2010 | Chang et al. |
| 2006/0004286 A1* | 1/2006 | Chang .................... A61B 90/16 |
| | | 600/435 |

(Continued)

FOREIGN PATENT DOCUMENTS

| EP | 3278760 A1 | 2/2018 |
| EP | 3277148 B1 | 8/2019 |

OTHER PUBLICATIONS

International Search Report and Written Opinion dated Jun. 23, 2020 for International Application No. PCT/IB2019/060448, 22 pages.

*Primary Examiner* — Deanna K Hall
(74) *Attorney, Agent, or Firm* — Frost Brown Todd LLC

(57) ABSTRACT

An instrument includes a handle assembly, a shaft, a dilation catheter, and a position sensor. The shaft extends distally from the handle assembly. The shaft includes a distal end that is configured to be introduced into an anatomical passageway within a head of a human. The dilation catheter includes an expandable dilator and is configured to advance distally relative to the shaft. The position sensor is configured to generate signals indicating a position of the position sensor within the head. The position sensor is configured to advance distally between at least first and second positions. The position sensor is disposed adjacent the distal end of the shaft in the first position, and is configured to be carried further distally by the dilation catheter to the second position. In the second position, the position sensor is separated a distance from the distal end of the shaft.

16 Claims, 11 Drawing Sheets

(51) Int. Cl.
  *A61B 34/20* (2016.01)
  *A61M 25/01* (2006.01)
  *A61B 1/06* (2006.01)
  *A61F 11/20* (2022.01)

(52) U.S. Cl.
  CPC .... *A61F 11/202* (2022.01); *A61M 2025/0166* (2013.01); *A61M 2205/8206* (2013.01)

(58) Field of Classification Search
  CPC ......... A61M 2025/09175; A61M 2025/09183; A61M 2210/0618; A61M 2210/0668; A61M 2210/0675; A61M 2210/0681; A61M 2210/1028; A61M 25/0136; A61M 2025/0175
  See application file for complete search history.

(56) References Cited

U.S. PATENT DOCUMENTS

| | | |
|---|---|---|
| 2010/0274188 A1 | 10/2010 | Chang et al. |
| 2011/0004057 A1 | 1/2011 | Goldfarb et al. |
| 2013/0274715 A1 | 10/2013 | Chan et al. |
| 2014/0364725 A1 | 12/2014 | Makower |
| 2016/0008083 A1 | 1/2016 | Kesten et al. |
| 2016/0310042 A1 | 10/2016 | Kesten et al. |
| 2017/0259048 A1* | 9/2017 | Matlock ................ A61M 29/02 |
| 2018/0036009 A1* | 2/2018 | Zoabi ................... A61B 5/6851 |
| 2018/0133438 A1 | 5/2018 | Hulvershorn et al. |
| 2018/0214216 A1 | 8/2018 | Sema et al. |
| 2018/0271590 A1* | 9/2018 | Basu ................... A61M 25/008 |
| 2018/0310886 A1 | 11/2018 | Salazar et al. |

\* cited by examiner

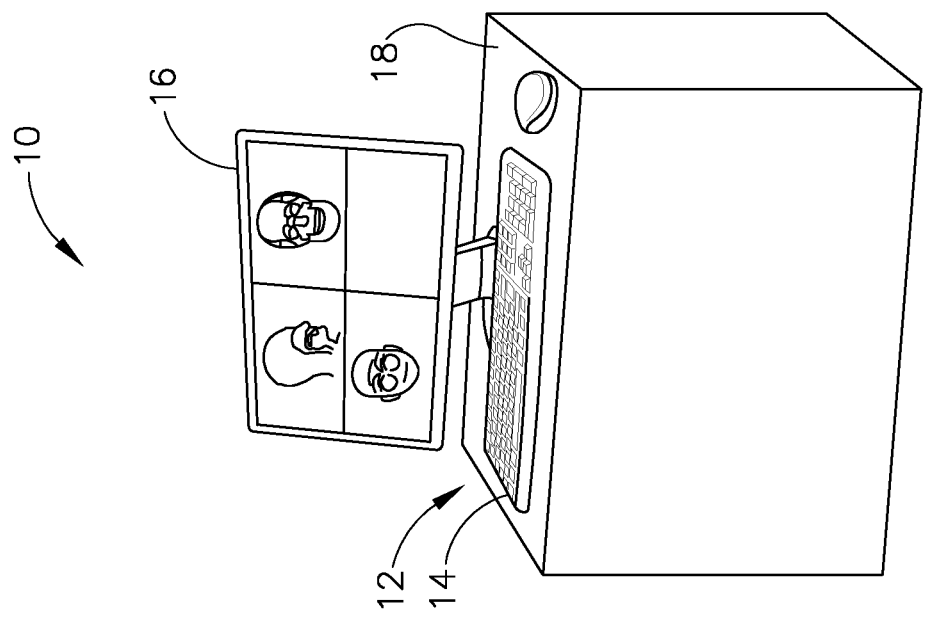
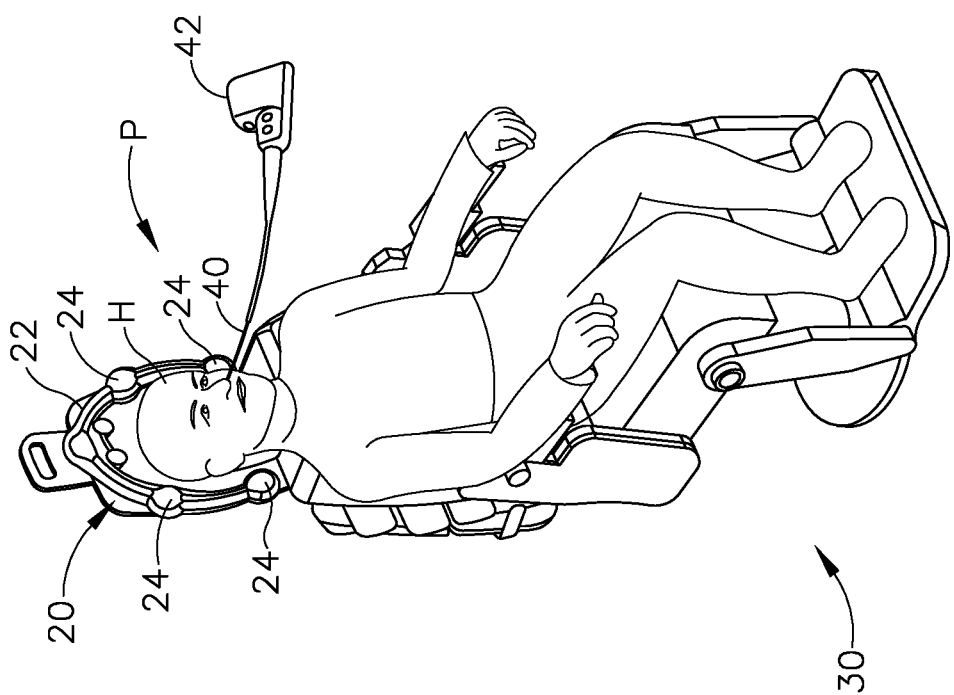
Fig. 1

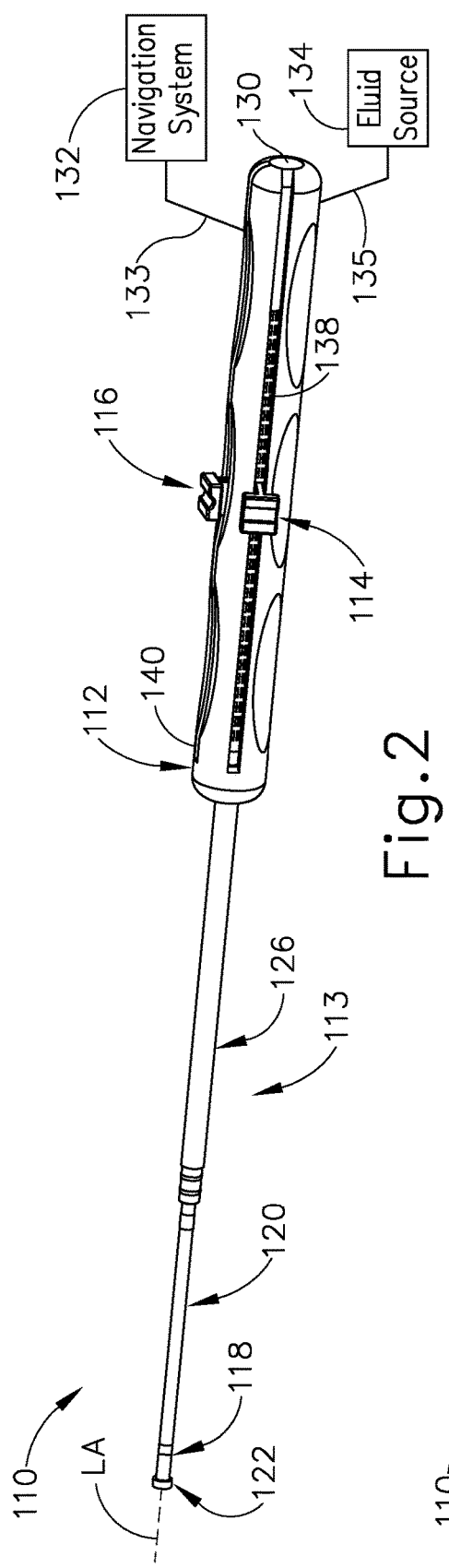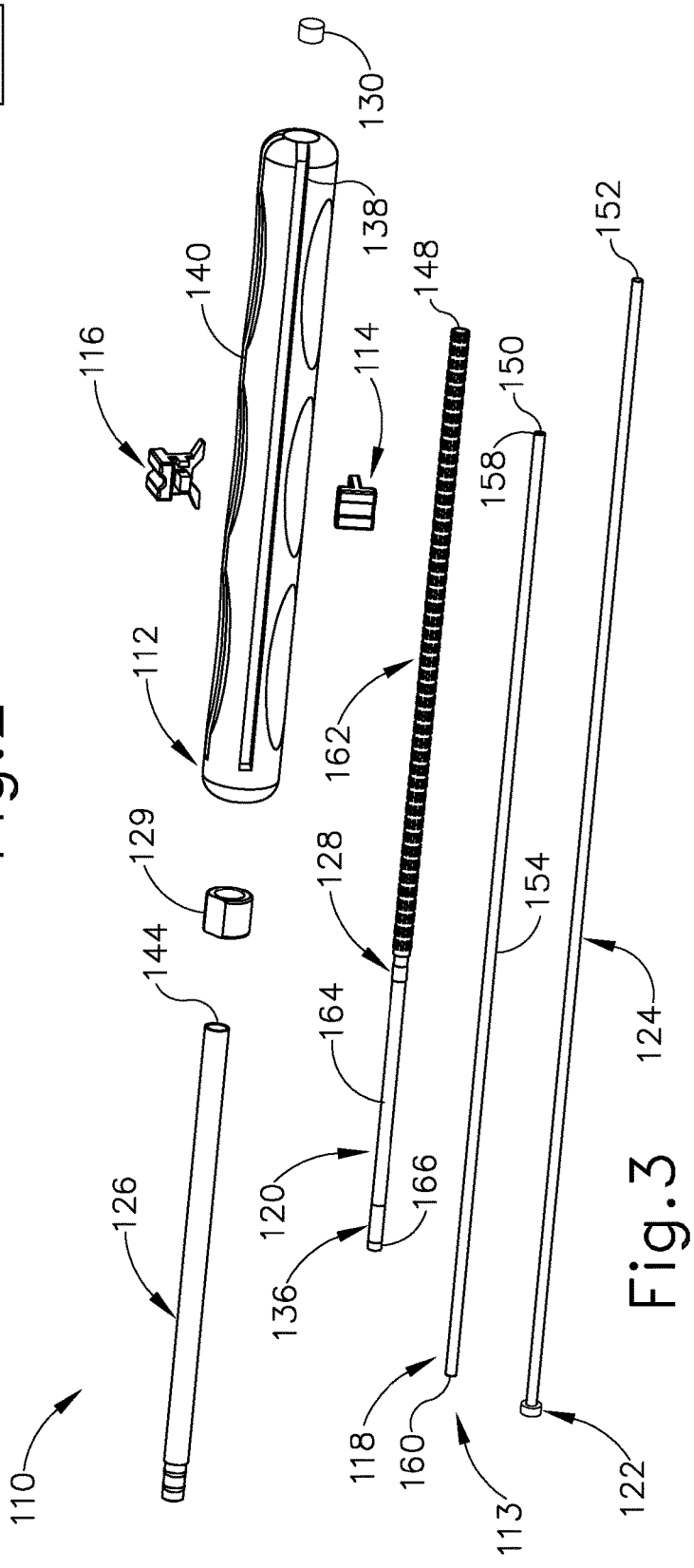

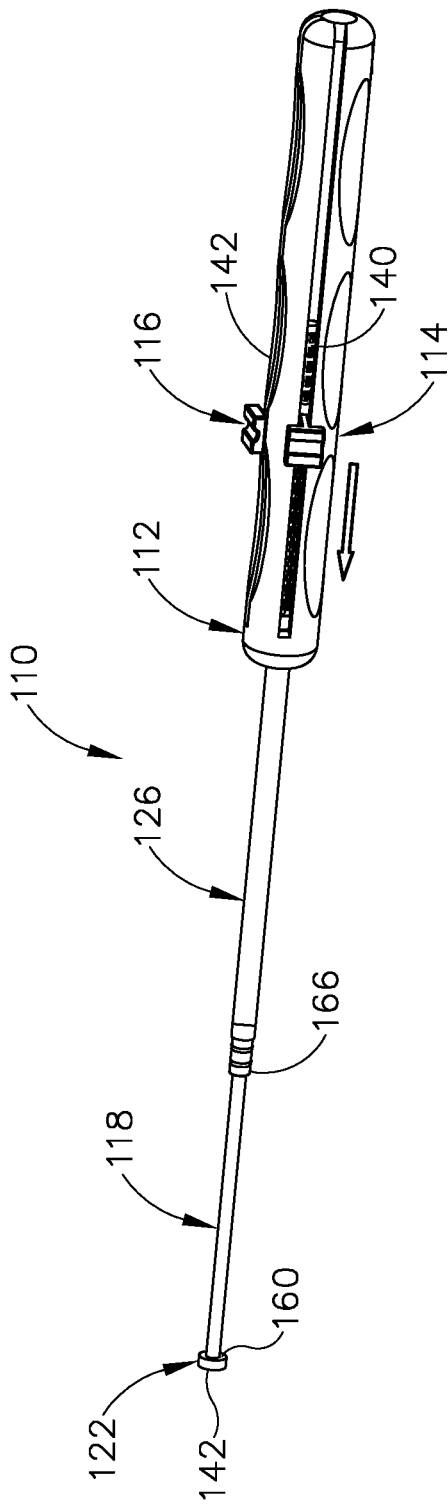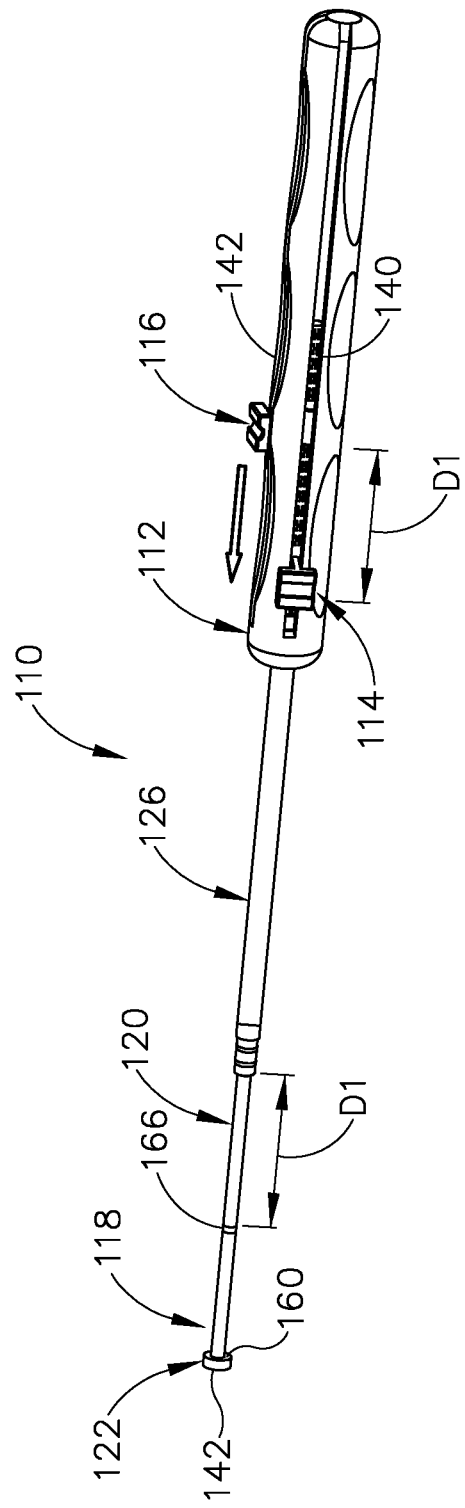
Fig.6A
Fig.6B

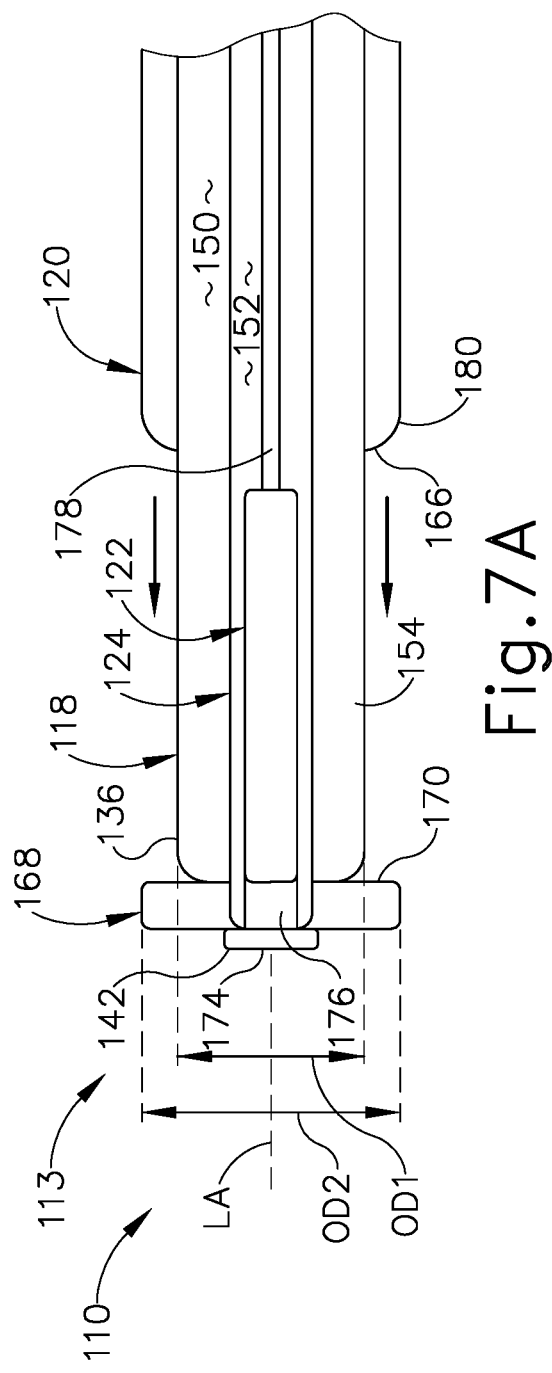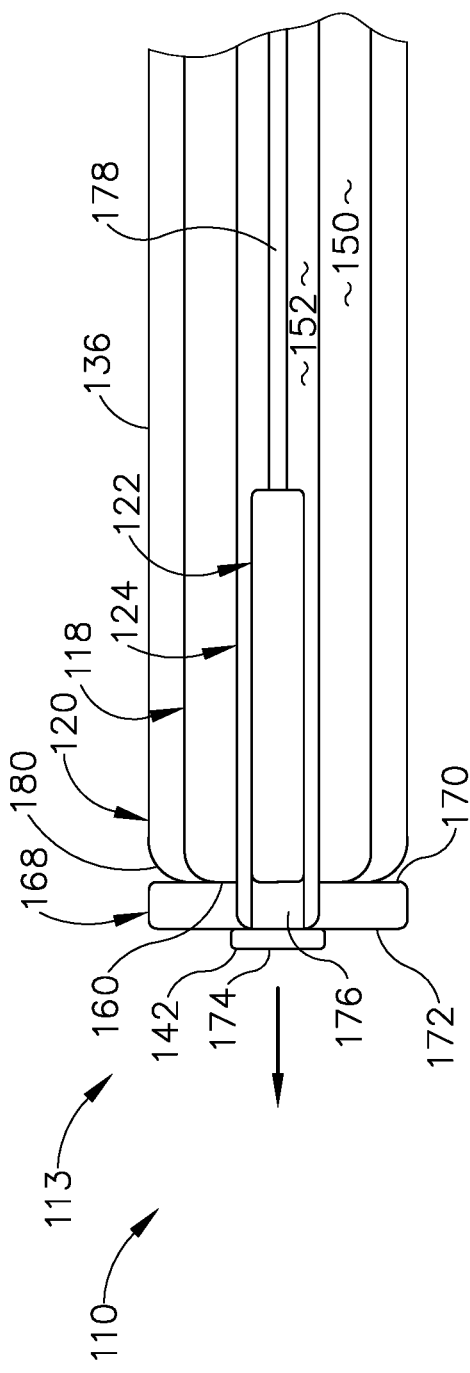

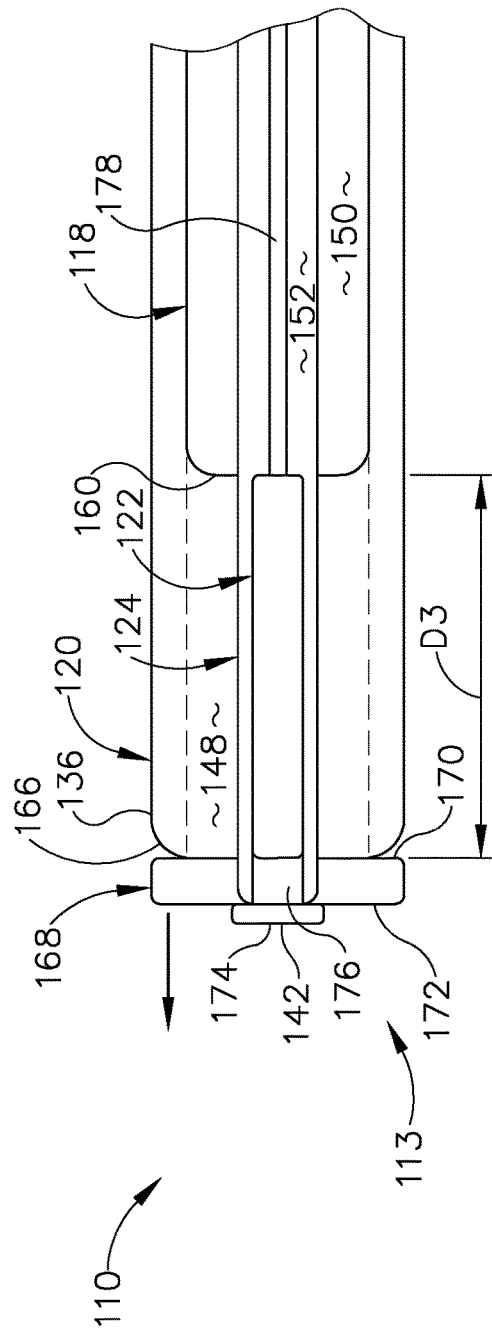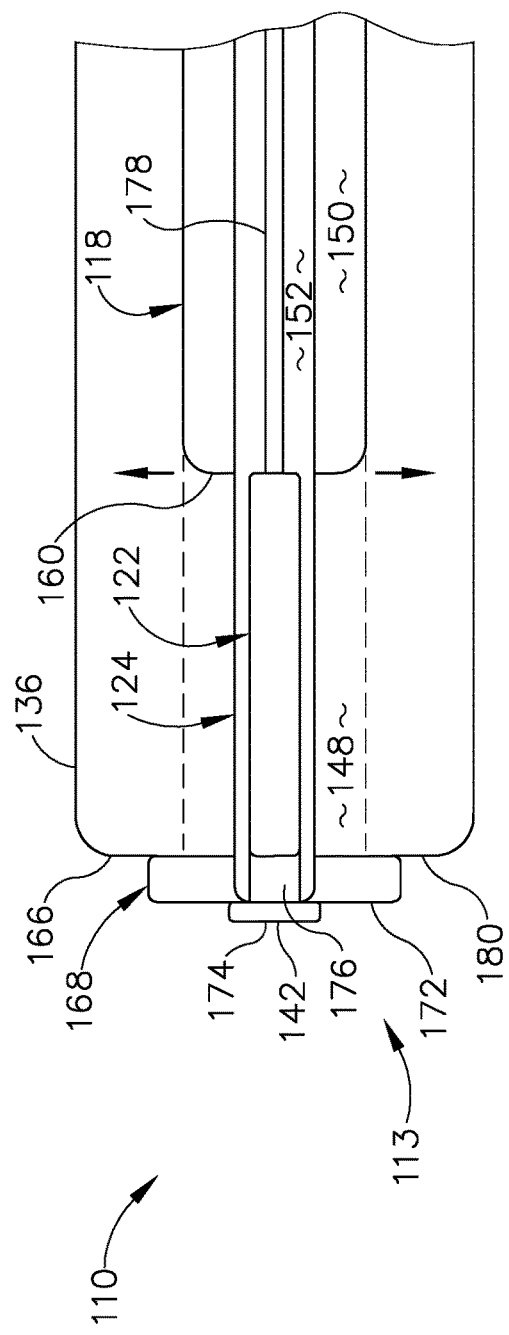

COMBINED SINUPLASTY AND SEEKER INSTRUMENT WITH NAVIGATION AND ILLUMINATION MODALITIES

PRIORITY

This application claims priority to U.S. Provisional Pat. App. No. 62/778,376, entitled "Combined Sinuplasty and Seeker Instrument with Navigation and Illumination Modalities," filed Dec. 12, 2018, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle ear and further provide improved drainage from the middle ear to the nasopharynx. Methods and devices for dilating the Eustachian tube are disclosed in U.S. Patent Pub. No. 2010/0274188, entitled "Method and System for Treating Target Tissue within the ET," published on Oct. 28, 2010, now abandoned, the disclosure of which is incorporated by reference herein; and U.S. Patent Pub. No. 2013/0274715, entitled "Method and System for Eustachian Tube Dilation," published on Oct. 17, 2013, now abandoned, the disclosure of which is incorporated by reference herein. An example of such a system is the Aera® Eustachian Tube Balloon Dilation System by Acclarent, Inc. of Irvine, Calif.

It may also be desirable to simply explore anatomical passageways in a patient. This may include ostia of paranasal sinuses, the larynx, the Eustachian tube, or other passageways within the ear, nose, or throat, etc. One method of exploring anatomical passageways includes using a passive seeker instrument or other kind of probe device that provides tactile feedback to the operator grasping a proximal end of the instrument.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, Calif. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs, an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 1 depicts a schematic view of an exemplary surgery navigation system being used on a patient seated in an exemplary medical procedure chair;

FIG. 2 depicts a perspective view of an exemplary instrument in a straight configuration;

FIG. 3 depicts an exploded perspective view of the instrument of FIG. 2, the instrument including a handle assembly, first and second sliders, an outer shaft, a dilation catheter, a rail, a position sensor, and a position sensor shaft;

FIG. 6A depicts a perspective view of the instrument of FIG. 2, with the position sensor positioned at the distal end of the rail;

FIG. 6B depicts a perspective view of the instrument of FIG. 6A, but with the dilation catheter partially advanced such that an expandable balloon of the dilation catheter overlies a proximal portion of the rail;

FIG. 7A depicts a side schematic view of a distal portion of the instrument of FIG. 6A with the position sensor positioned at the distal end of the rail and the dilation catheter being advanced distally;

FIG. 7B depicts a side schematic view of the distal portion of the instrument of FIG. 7A, but with a distal end of the dilation catheter positioned flush with a distal end of the rail;

FIG. 7C depicts a side schematic view of the distal portion of the instrument of FIG. 7B, but with the distal end of the dilation catheter carrying the position sensor distally away from the distal end of the rail, and with the expandable balloon of the dilation catheter in the contracted state;

FIG. 7D depicts a side schematic view of the distal portion of the instrument of FIG. 7C, but with the expandable balloon in the expanded state;

Figure 4:
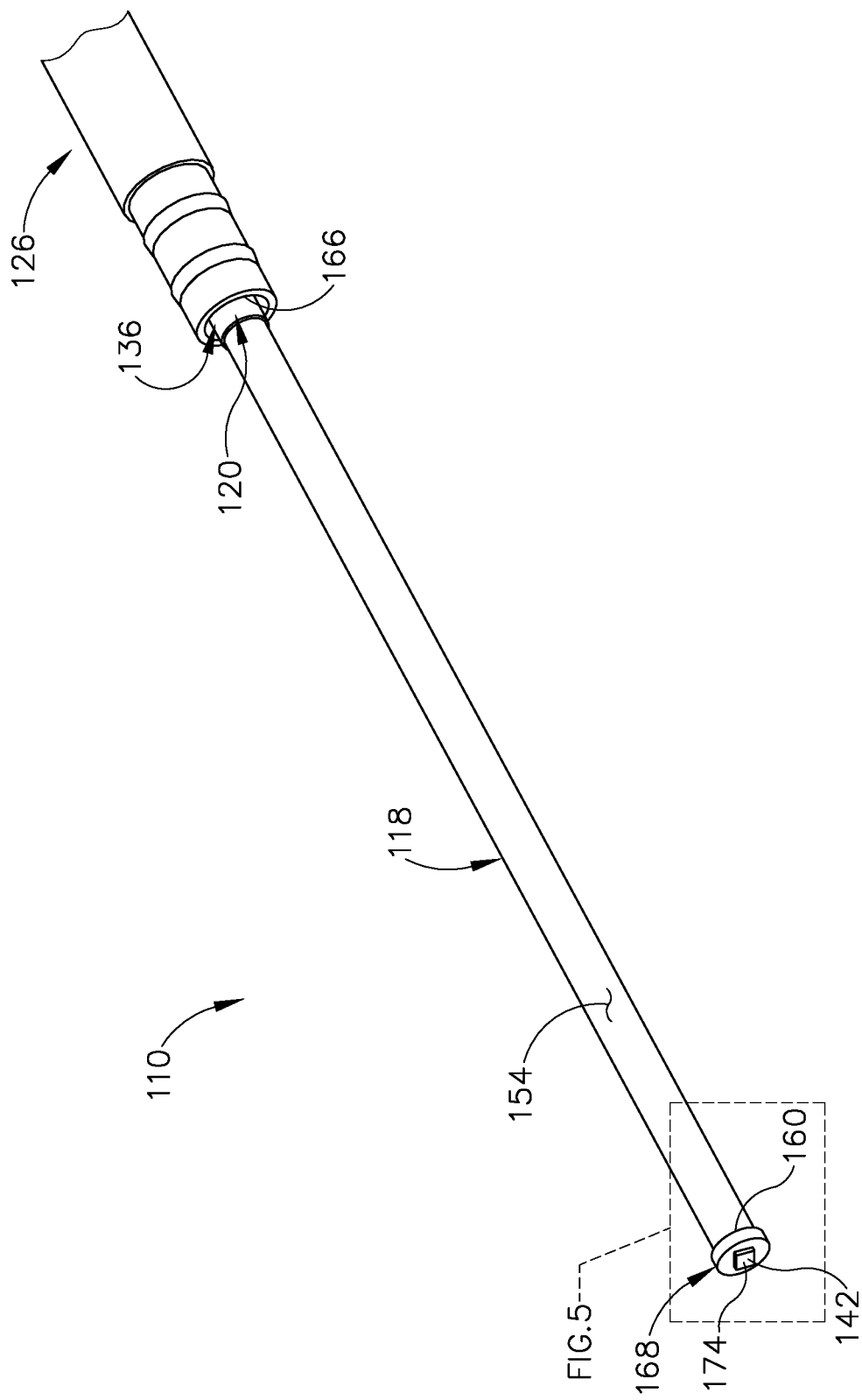
FIG. 4 depicts the position sensor of FIG. 2 disposed at a distal end of the rail.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description, serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. Exemplary Image Guided Surgery Navigation System

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein, IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (10) of the present example comprises a field generator assembly (20), which comprises a set of magnetic field generators (24) that are integrated into a horseshoe-shaped frame (22). Field generators (24) are operable to generate alternating magnetic fields of different frequencies around the head (H) of the patient (P). A navigation guidewire (40) is inserted into the head (H) of the patient (P) in this example. Navigation guidewire (40) may be a standalone device or may be positioned on an end effector or other location of a medical instrument such as a surgical cutting instrument or dilation instrument. In the present example, frame (22) is mounted to a chair (30), with the patient (P) being seated in chair (30) such that frame (22) is located adjacent to the head (H) of the patient (P). By way of example only, chair (30) and/or field generator assembly (20) may be configured and operable in accordance with at least some of the teachings of U.S. Pub. No. 2018/0310886, entitled "Apparatus to Secure Field Generating Device to Chair," published Nov. 1, 2018, issued as U.S. Pat. No. 10,561,370 on Feb. 18, 2020, the disclosure of which is incorporated by reference herein.

IGS navigation system (10) of the present example further comprises a processor (12), which controls field generators

(24) and other elements of IGS navigation system (10). For instance, processor (12) is operable to drive field generators (24) to generate alternating electromagnetic fields, and process signals from navigation guidewire (40) to determine the location of a sensor in navigation guidewire (40) within the head (H) of the patient (P). Processor (12) comprises a processing unit communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Navigation guidewire (40) includes a sensor (not shown) that is responsive to positioning within the alternating magnetic fields generated by field generators (24). A coupling unit (42) is secured to the proximal end of navigation guidewire (40) and is configured to provide communication of data and other signals between console (18) and navigation guidewire (40). Coupling unit (42) may provide wired or wireless communication of data and other signals.

In the present example, the sensor of navigation guidewire (40) comprises at least one coil at the distal end of navigation guidewire (40). When such a coil is positioned within an alternating electromagnetic field generated by field generators (24), the alternating magnetic field may generate electrical current in the coil, and this electrical current may be communicated along the electrical conduit(s) in navigation guidewire (40) and further to processor (12) via coupling unit (42). This phenomenon may enable IGS navigation system (10) to determine the location of the distal end of navigation guidewire (40) or other medical instrument (e.g., dilation instrument, surgical cutting instrument, etc.) within a three-dimensional space (i.e., within the head (H) of the patient (P), etc.). To accomplish this, processor (12) executes an algorithm to calculate location coordinates of the distal end of navigation guidewire (40) from the position related signals of the coil(s) in navigation guidewire (40). While the position sensor is located in guidewire (40) in this example, such a position sensor may be integrated into various other kinds of instruments, including those described in greater detail below.

Processor (12) uses software stored in a memory of processor (12) to calibrate and operate IGS navigation system (10). Such operation includes driving field generators (24), processing data from navigation guidewire (40), processing data from operating controls (14), and driving a display screen (16). In some implementations, operation may also include monitoring and enforcement of one or more safety features or functions of IGS navigation system (10). Processor (12) is further operable to provide video in real time via display screen (16), showing the position of the distal end of navigation guidewire (40) in relation to a video camera image of the patient's head (H), a CT scan image of the patient's head (H), and/or a computer-generated three-dimensional model of the anatomy within and adjacent to the patient's nasal cavity. Display screen (16) may display such images simultaneously and/or superimposed on each other during the surgical procedure. Such displayed images may also include graphical representations of instruments that are inserted in the patient's head (H), such as navigation guidewire (40), such that the operator may view the virtual rendering of the instrument at its actual location in real time. By way of example only, display screen (16) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein.

In the event that the operator is also using an endoscope, the endoscopic image may also be provided on display screen (16). The images provided through display screen (16) may help guide the operator in maneuvering and otherwise manipulating instruments within the patient's head (H) when such instruments incorporate navigation guidewire (40). It should also be understood that other components of a surgical instrument and other kinds of surgical instruments, as described below, may incorporate a sensor like the sensor of navigation guidewire (40).

II. Exemplary Instrument

In some conventional scenarios, an operator may use a seeker/pointer instrument for observing anatomical passageways and a separate balloon catheter instrument for dilating anatomical passageways within the head (H) of a patient (P). Using two separate instruments has drawbacks. As a result, it may be desirable to use a single instrument to both explore and dilate one or more anatomical passageways within the head (H) of a patient (P), including but not limited to a Eustachian tube, an ostium of a paranasal sinus, or other passageways associated with drainage of a paranasal sinus. It may also be desirable to utilize a system like IGS navigation system (10) to indicate the position of the distal end of the instrument in real time while within the head (H) of the patient (P). This may be accomplished by incorporating a position sensor into the instrument in a manner similar to that which guidewire (40) incorporates a position sensor as described above. It is further desirable to enable operation of the instrument comfortably using a single hand.

A. Exemplary Instrument in a Straight Configuration

FIGS. 2-11 depict an exemplary instrument (110) that solves these and other problems. As will be described in greater detail below, instrument (110) may integrate the functionality of a seeker/pointer instrument and a balloon catheter instrument enabling the combined benefits of both instruments to be realized. Instrument (110) may provide benefits including a low-profile ergonomic handle, single-handed advancement of an expandable balloon using multiple advancement mechanisms, conversion between a balloon sinuplasty device to dilate anatomical passageways and a pointer/seeker device to move tissue out of the way for advancement of expandable balloon, navigation using a position sensor disposed at the distal end of instrument (110), and illumination using a light source disposed at the distal end of instrument (110).

FIGS. 2-3 show perspective views of instrument (110) in a straight configuration. As shown in FIG. 2, instrument (110) includes a body (shown as a handle assembly (112)) and a shaft assembly (113) extending distally from handle assembly (112) along a longitudinal axis (LA). As shown in the exploded perspective view of FIG. 3, instrument (110) also includes first and second advancement mechanisms (shown as first and second sliders (114, 116)), a shaft (shown as a rail (118)), a dilation catheter (120), and a position sensor (122) (shown schematically in FIGS. 2-3). As shown in FIG. 3 and in greater detail with respect to FIGS. 7A-7D, shaft assembly (113) includes rail (118), a position sensor shaft (124), an outer shaft (126), and a dilation catheter shaft (128) of dilation catheter (120). Instrument (110) may additionally include a coupling (129) and a plug (130).

As shown in FIG. 2, instrument (110) is in signal communication with a navigation system (132) using a cable (133). Navigation system (132), which is similar to IGS navigation system (10) described above with reference to FIG. 1, enables an operator to visually determine the position of position sensor (122) within a 2-D or 3-D space using a display screen, similar to display screen (16). Instrument (110) is also in fluid communication with a fluid source (134) using one or more tubes (135) that are operable to fluidly inflate an expandable balloon (136) of dilation catheter (120).

As shown in FIGS. 2 and 3, handle assembly (112) is configured to be grasped by a single hand of an operator using a pencil grip, a power grip, or any other suitable kind of grip. Handle assembly (112) has a low-profile ergonomic shape for improved comfort and enhanced gripping by the operator. Handle assembly (112) includes first and second longitudinally extending channels (138, 140). As shown, first and second longitudinally extending channels (138, 140) are angularly offset by about 90-degrees and extend longitudinally along a majority of handle assembly (112). However, other arrangements of first and second longitudinally extending channels (138, 140) are also envisioned. First and second sliders (114, 116) are configured to move within respective first and second longitudinally extending channels (138, 140) of handle assembly (112). While first and second sliders (114, 116) are shown as being identical, first slider (114) may be different than second slider (116) if desired. It is also envisioned that additional sliders and corresponding channels may be incorporated. First and second sliders (114, 116) are described further with respect to FIGS. 6A-6C and 10A-10C.

Regarding the coaxial arrangement of shaft assembly (113) shown in FIGS. 3 and 7A-7D, a lumen (144) of outer shaft (126) is sized and configured to accommodate at least a portion of dilation catheter shaft (128). Similarly, a lumen (148) of dilation catheter shaft (128) is sized and configured to accommodate at least a portion of rail (118). Likewise, a lumen (150) of rail (118) is sized and configured to accommodate at least a portion of position sensor shaft (124). Likewise, a lumen (152) of position sensor shaft (124) is sized and configured to accommodate position sensor (122) as will be described in greater detail with reference to FIG. 5. As such, lumen (144) of outer shaft (126), lumen (148) of dilation catheter shaft (128), lumen (150) of rail (118), and lumen (152) of position sensor shaft (124) are each coaxially arranged (moving radially inward) along longitudinal axis (LA).

As shown in FIGS. 2-5, rail (118) extends distally from handle assembly (112) and includes an exterior surface (154) and an interior surface (156) (see FIGS. 7A-7D) that defines lumen (150). Additionally, rail (118) includes opposing proximal and distal ends (158, 160). Distal end (160) of rail (118) is configured to be introduced into an anatomical passageway within head (H) of the patient (P). FIGS. 2-3 show rail (118) in a straight configuration, while FIG. 11 shows rail (118) in a bent configuration. Dilation catheter (120) includes dilation catheter shaft (128) having proximal and distal portions (162, 164). As shown, expandable balloon (136) is disposed at a distal end (166) of dilation catheter (120). Expandable balloon (136) is configured to expand when fluid is introduced by fluid source (134) through tube (135) into expandable balloon (136). Conversely, expandable balloon (136) is configured to contract when fluid is removed from expandable balloon (136) through tube (135). Expandable balloon (136) is configured to advance distally around exterior surface (154) of rail (118). As will be described in greater detail below with reference to FIGS. 10A-10C, proximal portion (162) of dilation catheter shaft (128) is non-smooth while distal portion (164) is generally smooth.

Figure 5:
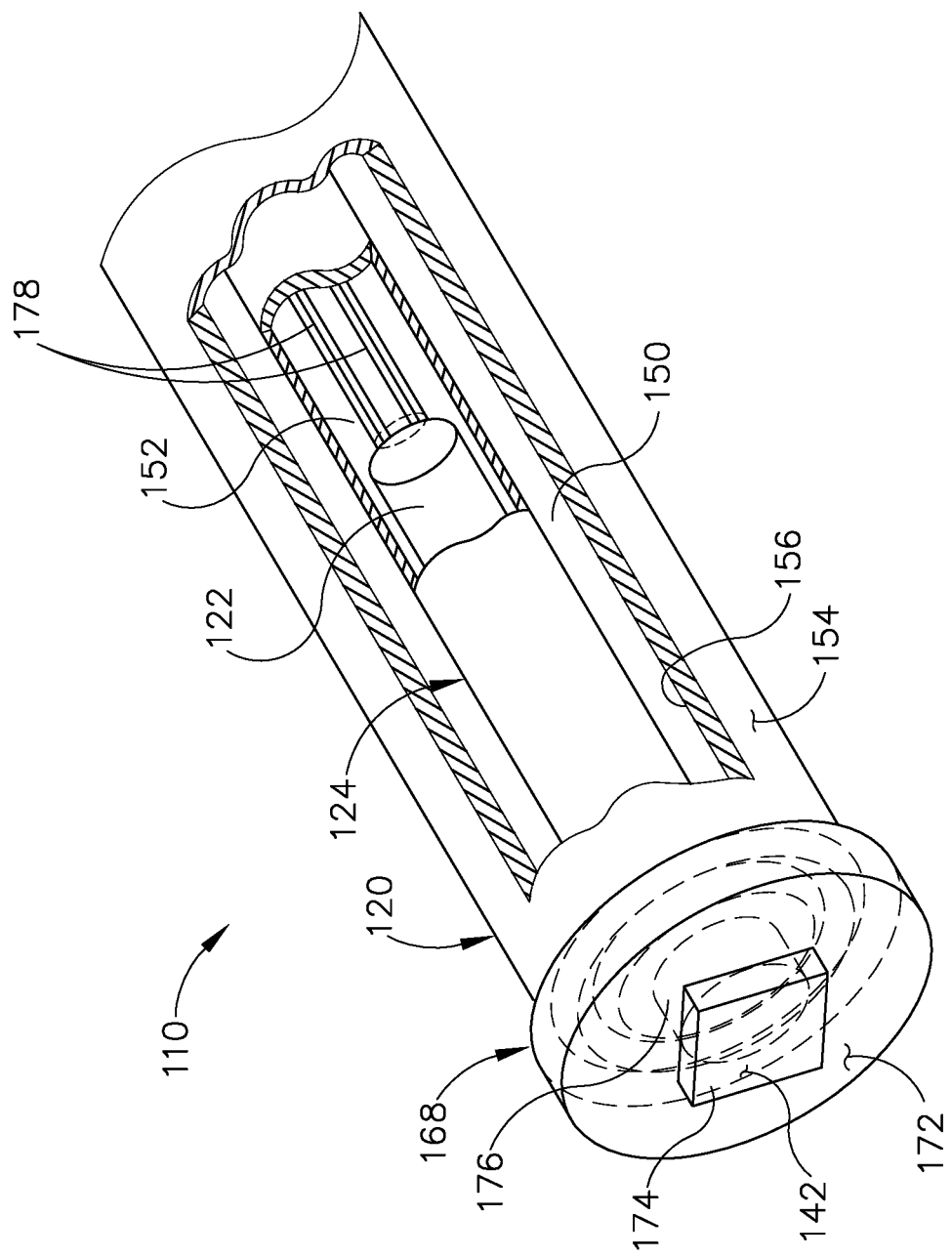
FIG. 5 depicts a detailed cutaway portion of the distal end of the rail of FIG. 4, the cutaway portion revealing the position sensor shaft that also includes a cutaway portion to reveal the position sensor and accompanying wires.

FIG. 4 shows position sensor (122) disposed at distal end (160) of rail (118), similar to FIG. 2. Position sensor (122) is configured to generate signals indicating a specific location of distal end (142) of instrument (110) (e.g. within head (H) of patient (P)). As shown in FIGS. 4 and 5, instrument (110) includes a disc (168), shaped as a circular plate. Disc (168) includes proximal and distal surfaces (170, 172). As shown, proximal surface (170) of disc (168) is in contact with position sensor (122). As will be described below with reference to FIGS. 6A-7D, disc (168) may be fixably coupled with at least one of position sensor (122) or position sensor shaft (124) such that when disc (168) moves distally, position sensor shaft (124) or at least position sensor (122) also moves distally. Conversely, when disc (168) moves proximally, position sensor shaft (124) or at least position sensor (122) also moves proximally. However, it is also envisioned that disc (168) may be indirectly coupled with position sensor (122) or position sensor shaft (124).

As shown in FIGS. 4-5, distal surface (172) of disc (168) is adjacent a light source to provide light at distal end (142) of instrument (110). As shown, the light source is a light emitting diode ("LED") (174); however, a variety of other light sources are also envisioned. As shown, battery is in direct contact with LED (174). While LED (174) is shown as being in direct contact with distal surface (172) of disc (168), it is also envisioned that LED (174) may be in indirect contact with distal surface (172) of disc (168) and separated by a distance. LED (174) may include a battery (176) positioned near LED (174) or be powered by a power source within handle assembly (112) or a power source external to instrument (110). As shown, battery (176) is positioned distally of position sensor (122) within disc (168); however, it is also envisioned that battery (176) may be positioned distally of disc (168). Using LED (174) provides a low-cost method of illumination. This aids in navigation of distal end (142) of instrument (110) either for distal end (160) of rail (118) when used as a pointer instrument or for distal end (166) of dilation catheter (120) when used for balloon sinuplasty instrument.

Powering LED (174) using battery (176) positioned directly adjacent or near LED (174) eliminates the additional space needed for a fiber optic light source, which enables placement of position sensor (122) directly proximal to or near LED (174). Illumination using LED (174) and position sensing using position sensor (122) provide additional confidence to the operator in determining whether distal end (160) of rail (118) or distal end (166) of dilation catheter (120) is properly positioned. In addition to potentially providing transillumination effects (like an illuminating guidewire), LED (174) disposed on disc (168) at distal end (142) of instrument (110) may also provide additional enhanced illumination of the field of view of an endoscope that is inserted in the nasal cavity of patient (P). LED (174) can reach places that the endoscope cannot physically reach (but can still be viewed by the endoscope). Thus, even if the endoscope has its own integral light source, this additional light source (e.g. LED (174)) may be advanced further into the nasal cavity of the endoscope's light source, thereby providing the endoscope with a better-illuminated view of hard-to-reach places.

FIG. 5 shows a detailed cutaway portion of distal end (160) of the rail (118) of FIG. 4, the cutaway portion revealing position sensor shaft (124), where lumen (152) of position sensor shaft (124) accommodates position sensor (122) and one or more wires (178). Wires (178) extend proximally from position sensor (122) through lumen (152) and handle assembly (112) to cable (133). This provides a path for communication of position-indicative signals from position sensor (122) to cable (133) coupled with navigation system (132) which is similar to IGS navigation system (10).

In the present example, position sensor (122) comprises a wire coil wrapped about an axis that is coaxial with longitudinal axis (LA). In some variations, position sensor (122) comprises two or more wire coils that are wrapped about respective axes that are orthogonal to each other. Cable (133) may be further coupled with processor (12) of IGS navigation system (10) in any suitable fashion, thereby enabling position-indicative signals from position sensor (122) to reach processor (12). When position sensor (122) is positioned within an alternating electromagnetic field generated by field generators (24), the alternating magnetic field may generate electrical current in position sensor (122), and this electrical current may be communicated along the wire(s) (178) in position sensor shaft (124) and handle assembly (112) to cable (133) and further to processor (12). This phenomenon may enable IGS navigation system (10) to determine the location of position sensor (122) within a three-dimensional space (i.e., within the head (H) of the patient (P), etc.). To accomplish this, processor (12) executes an algorithm to calculate location coordinates of position sensor (122) from the position related signals of position sensor (122).

It should be understood that an operator may advance position sensor (122) into various passageways within a head (H) of a patient (P) and receive real-time feedback on the location of position sensor (122) within the head (H) of the patient (P). The operator may thus maneuver distal end (160) of rail (118) and/or distal end (166) of dilation catheter (120) to explore various passageways within a head (H) of a patient (P) in the context of visualization that is provided via display screen (16) of IGS navigation system (10). In some versions, handle assembly (112) includes one or more buttons or other user input features that enable the operator to selectively mark points in the anatomy as the operator maneuvers distal end (142) through the anatomy. When the operator actuates such buttons or other user input features, processor (12) may save the particular location of distal end (160) of rail (118) or distal end (166) of dilation catheter (120) within head (H) of patient (P) at the time the button or other user input feature was actuated. Display screen (16) may also prompt the operator to enter an annotation or other note to provide further information in association with the marked location. In some versions, handle assembly (112) or a connector at the free end of cable (133) includes an EEPROM or other storage device that is configured to store calibration data associated with calibration of instrument (110) relative to IGS navigation system (10).

B. Exemplary Operation of Instrument

Figure 6C:
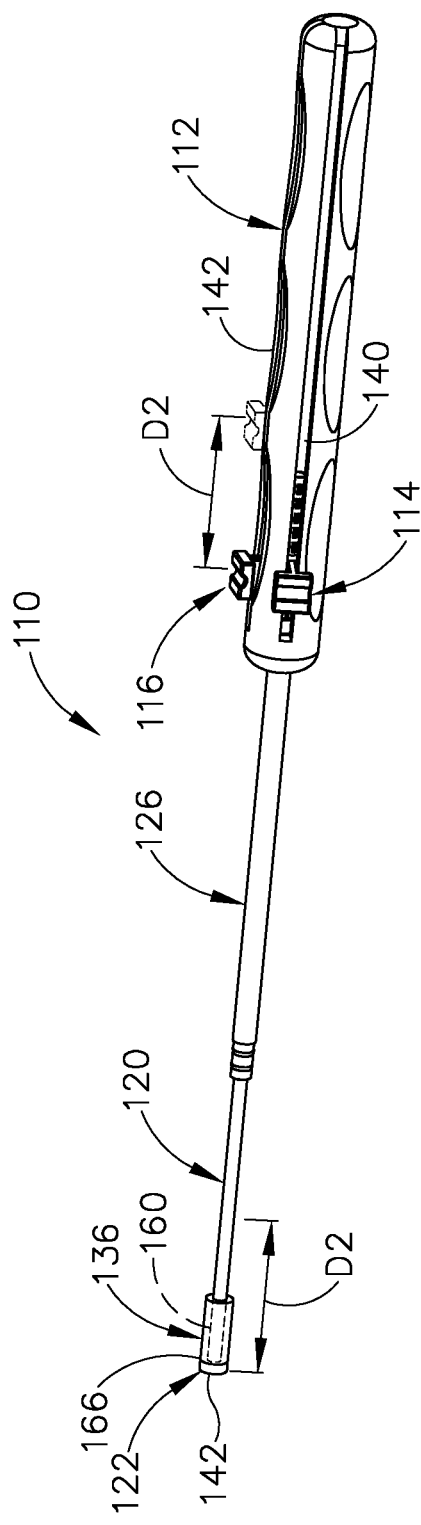
FIG. 6C depicts a perspective view of the instrument of FIG. 6B, but with the position sensor positioned at a distal end of the dilation catheter and the dilation catheter fully advanced, and with the expandable balloon in a contracted state.

FIGS. 6A-7D show an exemplary method of operating instrument (110), where longitudinal movement of first and second sliders (114, 116) cause longitudinal movement of expandable balloon (136) of dilation catheter (120) relative to distal end (160) of rail (118). FIGS. 6A-6B each show a first position of position sensor (122), where position sensor (122) is disposed adjacent distal end (160) of rail (118). In the first position, distal end (166) of dilation catheter (120) is positioned proximal to distal end (160) of rail (118). In FIG. 6B, while still in the first position, expandable balloon (136) of dilation catheter (120) is advanced distally a first distance (D1) circumferentially around exterior surface (154) of rail (118) by an operator moving first slider (114) distally the first distance (D1). Distal end (166) of dilation catheter (120), including a portion of expandable balloon (136), circumferentially overlies a portion of rail (118). In FIG. 6A instrument (110) may be used as a straight pointer instrument with expandable balloon (136) generally hidden by outer shaft (126), while in FIGS. 6B-6D, instrument (110) may be used as a balloon sinuplasty device since expandable balloon (136) is not hidden by outer shaft (126) and may expand when desired.

FIGS. 7A-7B show side schematic views of position sensor (122) positioned at distal end (160) of rail (118). As shown in FIG. 7A, position sensor (122) is operatively coupled to disc (168) having a first outer diameter (OD1) that is greater than a second outer diameter (OD2) of rail (118), such that expandable balloon (136) is configured to advance distally around exterior surface (154) of rail (118). It is also envisioned that disc may be omitted, such that first outer diameter (OD1) of another structure (e.g. LED (174) or disc position sensor (122)) is slightly greater than outer diameter (OD2) of rail (118), such that a portion of dilation catheter (120) (e.g. expandable balloon (136)) catches on this structure. FIG. 7B shows a side schematic view of instrument (110) of FIG. 7A, but with distal end (166) of dilation catheter (120) positioned flush with distal end (160) of rail (118). In other words, FIG. 7B shows expandable balloon (136) of dilation catheter (120) is positioned further distally than FIG. 6B. This point is considered the "hand off position" for position sensor (122), because position sensor (122) transitions at this point to become operatively coupled with distal end (166) of dilation catheter (120) when distal end (166) of dilation catheter (120) is advanced distally beyond distal end (160) of rail (118).

FIGS. 6C and 7C show position sensor (122) carried distally by dilation catheter (120) to a second position, such that distal end (166) of dilation catheter (120) is positioned distal to distal end (160) of rail (118). As shown in FIG. 6C, second slider (116) advances within second longitudinally extending channel (140). This causes dilation catheter (120) to carry position sensor (122) distally beyond distal end (160) (shown using a dashed lead line in FIG. 6C) of rail (118). As shown with respect to FIGS. 6B, 6C, and 7C, first slider (114) advances expandable balloon (136) a first distance (D1) and second slider (116) advances expandable balloon (136) a second distance (D2), such that distal end (166) of dilation catheter (120) is advanced distally beyond distal end (160) of rail (118) by a third distance (D3). First slider (114) may advance expandable balloon (136) the same distance or a different distance relative to second slider (116). In the second position shown in FIG. 7C, position sensor (122) is separated from distal end (160) of rail (118) by a third distance (D3), such that distal end (142) of instrument (110) is generally adjacent distal end (166) of dilation catheter (120).

In moving from the first position to the second position, a portion of dilation catheter (120), shown as a distal end (180) of expandable balloon (136), actually carries, or otherwise pushes, position sensor (122) distally to the second position. It is envisioned that another portion of dilation catheter (120) may carry position sensor (122) distally. The operator may advance either of first or second sliders (114, 116) independently. As shown in FIG. 6C, expandable balloon (136) is not fully distally advanced until both of first and second sliders (114, 116) are fully advanced on handle assembly (112). First and second sliders (114, 116) are configured to be operated using a single hand, since the cumulative distance first and second sliders (114, 116) travel is halved through the use of two sliders instead of a single slider. This allows a single hand to control both first and second sliders (114, 116). The operator may first advance first slider (114) and then second slider (116), or alternatively, the operator may advance second slider (116) then first slider (114). However, as shown, each of first and second sliders (114, 116) only advance expandable balloon (136) partially.

Figure 6D:
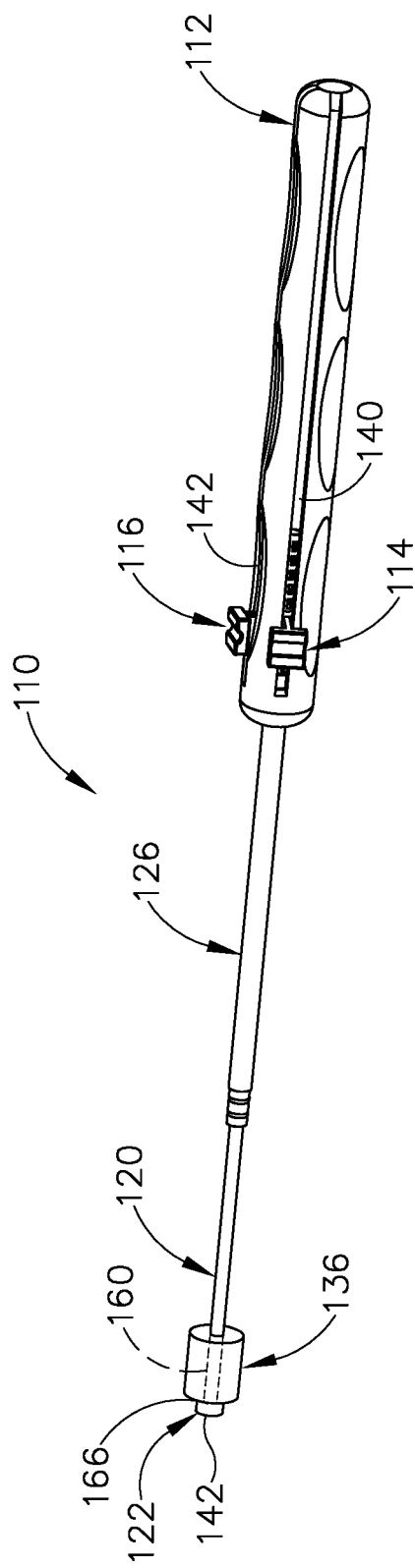
FIG. 6D depicts a perspective view of the instrument of FIG. 6C, but with the expandable balloon in an expanded state.

FIG. 6D shows a perspective view of instrument (110) of FIG. 6C, but with expandable balloon (136) in an expanded state. Similarly, FIG. 7D shows a side schematic view of instrument (110) of FIG. 7C, also in the expanded state. As previously described, expandable balloon (136) is configured to expand when fluid is introduced by fluid source (134) through tube (135) into expandable balloon (136). Conversely, expandable balloon (136) is configured to contract when fluid is removed through tube (135). While not shown, it is envisioned that proximal and distal ends of expandable balloon (136) may be tapered. An image guided surgery system displays position of position sensor (122) in head (H) of patient (P) in real time, based on signals from position sensor (122).

C. Exemplary Advancement Mechanism

Figure 8:
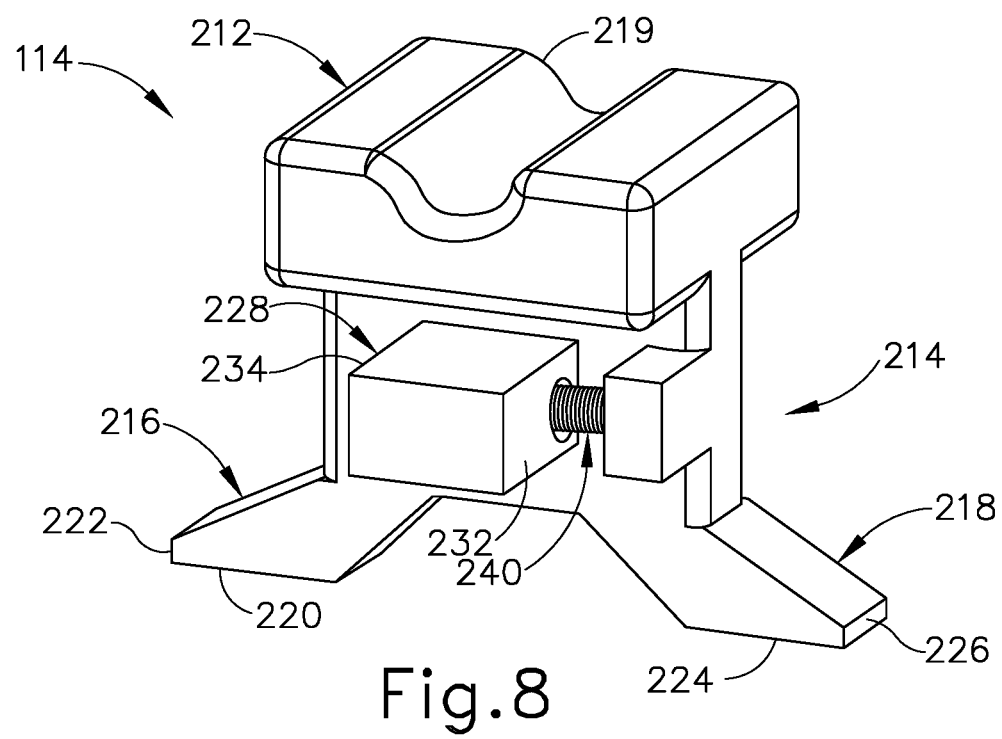
FIG. 8 depicts an enlarged perspective view of the first slider of FIG. 2.
Figure 9:
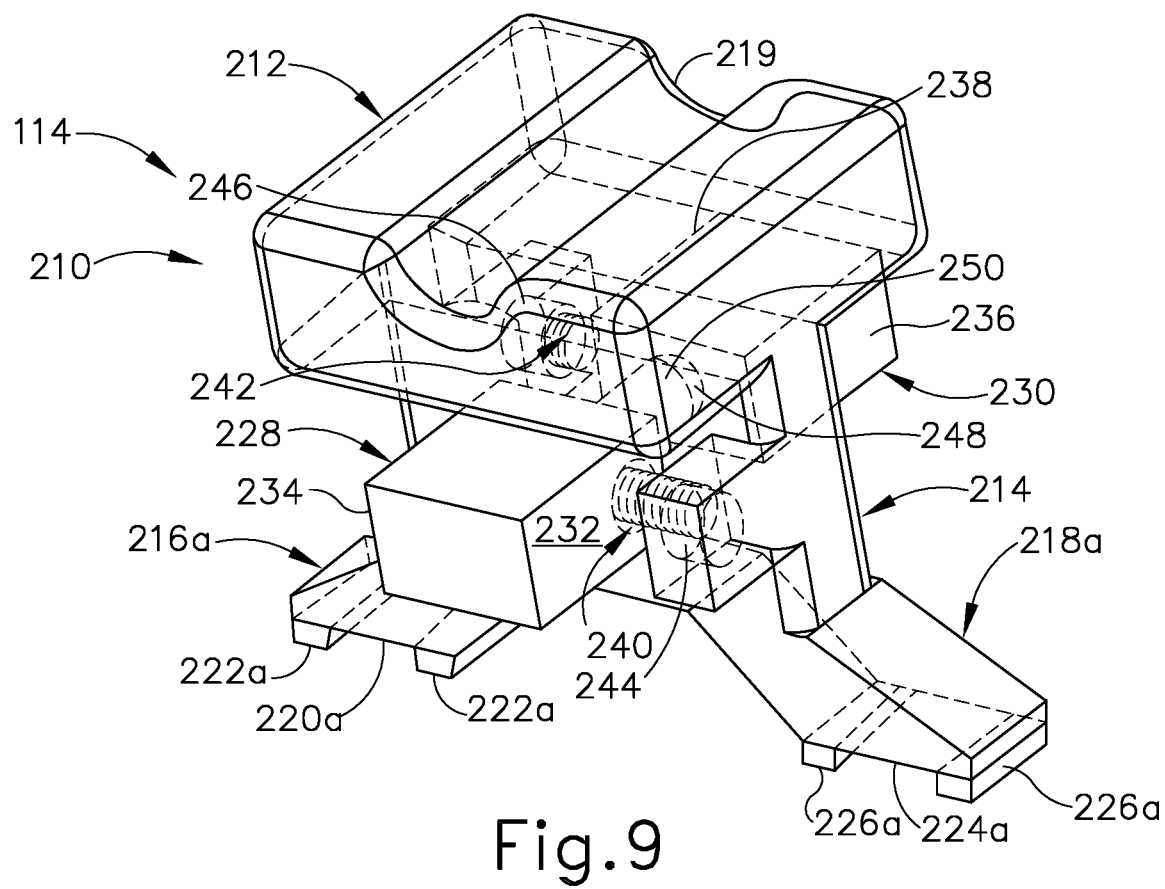
FIG. 9 depicts another perspective view of the slider of FIG. 8, but with features obstructed from view being shown in phantom.

FIGS. 8-9 show enlarged perspective views of first slider (114) of FIG. 2. As described above, first slider (114) moves dilation catheter shaft (128) relative to distal end (160) of rail (118). While FIGS. 8-9 are described below with respect to first slider (114), the below description also applies to second slider (116) that moves dilation catheter shaft (128) relative to distal end (160) of rail (118). As shown in FIG. 8, first slider (114) includes a body (210) that includes a head portion (212), a middle portion (214), and distal and proximal pawls (216, 218). Head portion (212) includes a recessed central portion (219) enabling an operator's finger to more easily locate and subsequently advance first slider (114). Distal pawl (216) includes a bottom surface (220) and a distal engagement feature, shown as a distal lateral surface (222) of distal pawl (216). Similarly, proximal pawl (218) includes a bottom surface (224) and a proximal engagement feature, shown as a proximal lateral surface (226) of proximal pawl (218).

As shown in FIGS. 8-9, first slider (114) additionally includes first and second oppositely disposed rails (228, 230). First rail (228) includes proximal and distal surfaces (232, 234). Similarly, second rail (230) includes proximal and distal surfaces (236, 238). First slider (114) includes first and second springs (240, 242) disposed at least partially within cavities (244, 246) of first and second rails (228, 230). As shown in FIG. 9, first rail (228) is connected to second rail (230) using a pin (248). In other words, pin (248) fixably couples first and second rails (228, 230) together. Pin (248) is disposed in an aperture (250) of body (210). This arrangement enables relative movement between body (210) and first and second rails (228, 230), such that first and second rails (228, 230) may maintain a horizontal orientation along a longitudinal axis (LA1) of dilation catheter (120) shown in FIGS. 10A-10C. Aperture (250) and pin (248) are sized to enable body (210) to pivot relative to first and second rails (228, 230), about the longitudinal axis of pin (248). Pin (248) may be integrally coupled with both of first and second rails (228, 230), one of first and second rails (228, 230), or subsequently coupled with first and second rails (228, 230) during assembly (e.g. using a threaded connection or other suitable connection structure).

With regard to FIG. 9, first slider (114) includes different distal and proximal engagement features of distal and proximal pawls (216a, 218a). More specifically, FIG. 9 shows distal pawl (216a) as including a bottom surface (220a) and a distal engagement feature, shown as teeth (222a), and proximal pawl (218a) as including a bottom surface (224a) and a proximal engagement feature, shown as teeth (226a). First and second springs (242) are configured to cause either proximal engagement feature (e.g. distal lateral surface or teeth (222, 222a)) or proximal engagement feature (proximal lateral surface or teeth (226, 226a)) to engage exterior of dilation catheter (120). Teeth (222a, 226a) may have a variety of different shapes, and may include any number of suitable teeth. It is also envisioned that distal and proximal pawls (216a, 218a) include respective distal and proximal lateral surfaces (222, 226) to engage dilation catheter shaft (128).

Figure 10A:
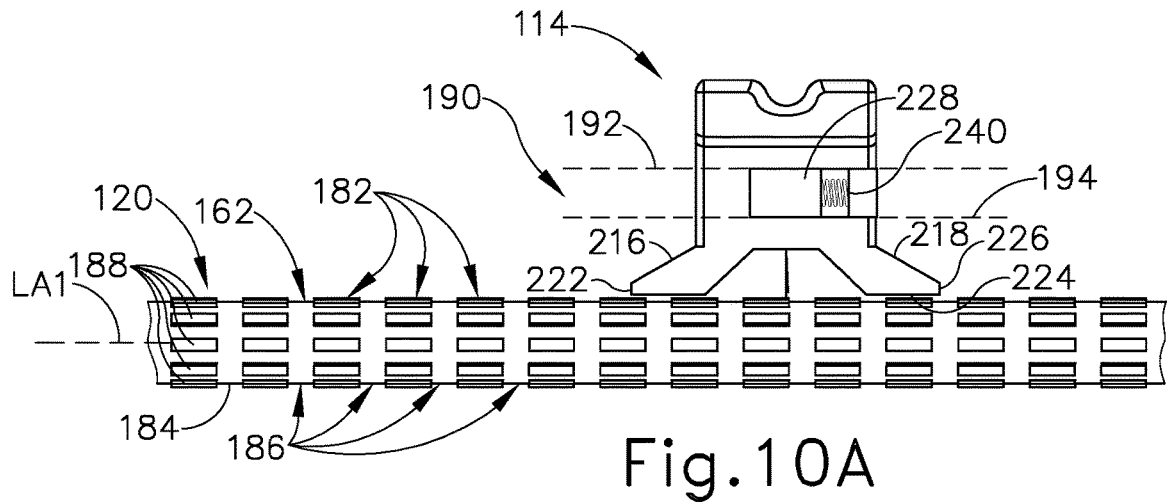
FIG. 10A depicts a side elevational view of the slider of FIG. 8 and the dilation catheter of FIG. 3, with the first slider in a neutral state, where distal and proximal pawls of the first slider are not engaged with corresponding grooves of the dilation catheter.
Figure 10B:
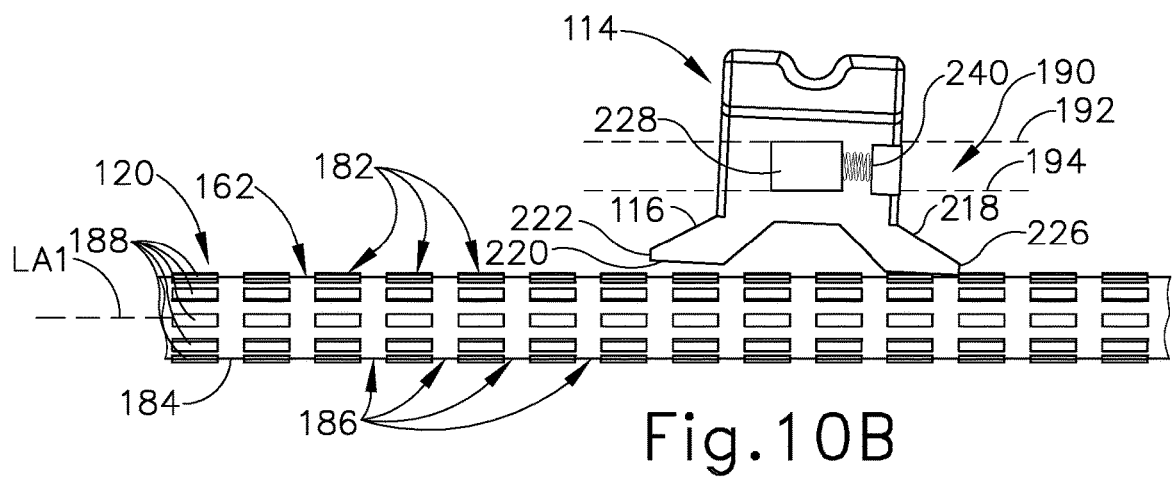
FIG. 10B depicts a side elevational view of the slider of FIG. 8 and the dilation catheter of FIG. 3, with the first slider being advanced distally, where the distal and proximal pawls of the first slider are engaged with the grooves of the dilation catheter.
Figure 10C:
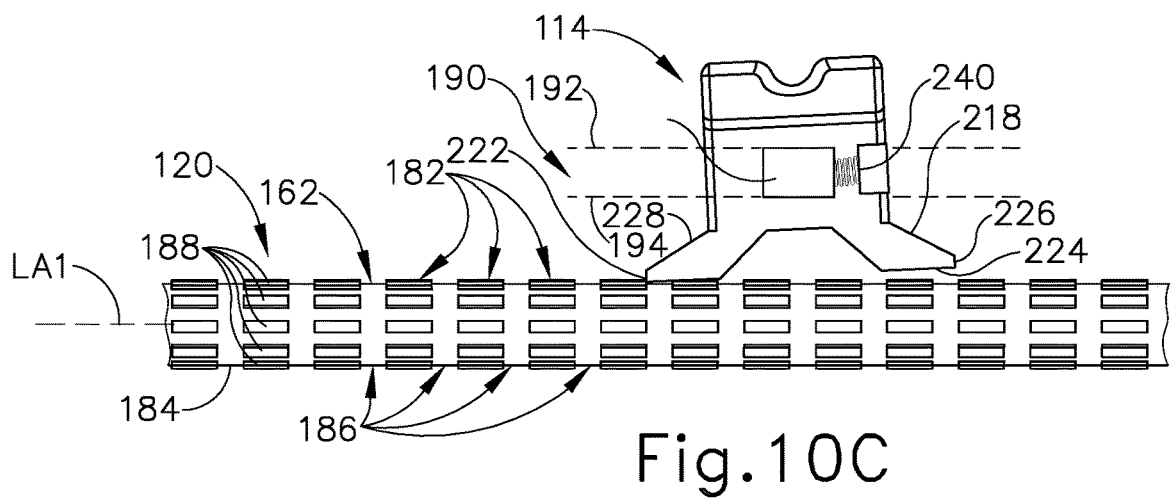
FIG. 10C depicts a side elevational view of the slider of FIG. 8 and the dilation catheter of FIG. 3, with the slider being retracted proximally distally, where the distal and proximal pawls of the slider are engaged with the grooves of the dilation catheter.
Figure 11:
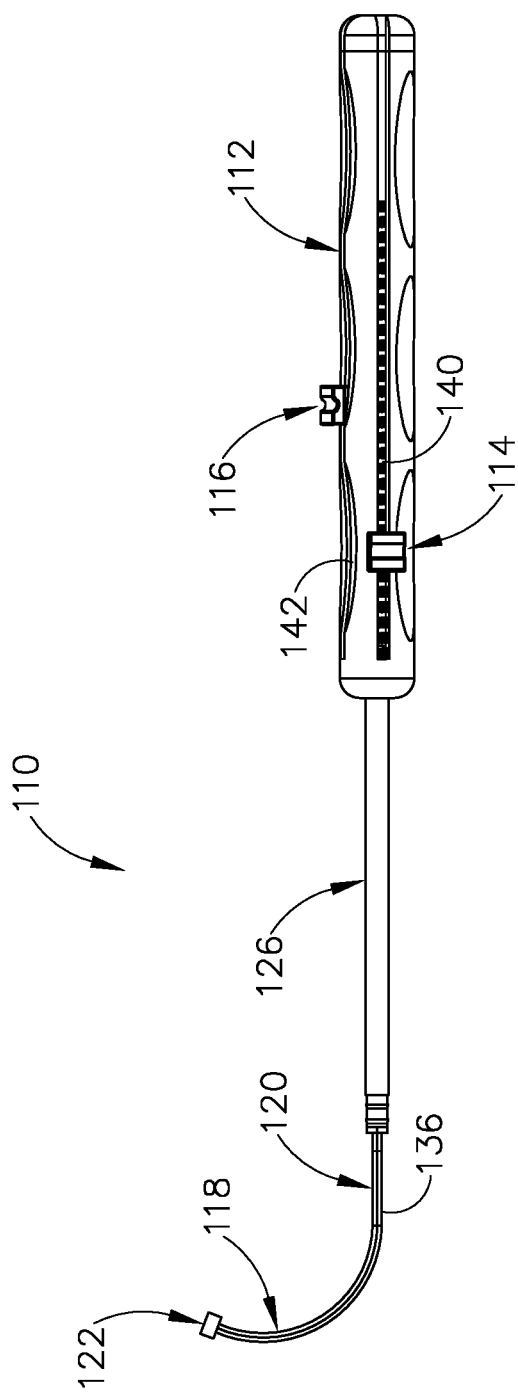
FIG. 11 depicts a side elevational view of the instrument of FIG. 2, but with a distal portion of the rail in a bent configuration.

FIGS. 10A-10C show an exemplary method of advancing and retracting dilation catheter shaft (128) as described above to move expandable balloon (136) relative to distal end (160) of rail (118). While FIGS. 10A-10C are described with respect to first slider (114), these aspects apply equally to second slider (116) that also moves expandable balloon (136) relative to distal end (160) of rail (118). As shown in FIGS. 10A-10C, proximal portion (162) of dilation catheter shaft (128) includes a plurality of annular arrays (182) disposed longitudinally along an exterior (184) of proximal portion (162). Two adjacent annular arrays (182) define an annular groove (186) configured to receive distal or proximal pawl (216, 216a, 218, 218a) as described below. However, other arrangements of annular grooves (186) are also envisioned. Each annular array (182) includes a plurality of spaced projections (188). As shown, spaced projections (188) are equally spaced around the circumference of proximal portion (162).

FIG. 10A shows first slider (114) in a neutral state, where distal and proximal pawls (216, 218) of first slider (114) are not actively engaged with corresponding annular grooves (186) of dilation catheter (120). In other words, distal and proximal pawls (216, 218) of first slider (114) are separated a distance from annular grooves (186). Instrument (110) ensures that when first or second sliders (114, 116) are moved, dilation catheter (120) also moves by being either advanced or retracted. This movement is achieved by integrating first and second springs (240, 242) into first and second sliders (114, 116) to keep first and second sliders (114, 116) disengaged from dilation catheter (120) in the neutral state when not being actively advanced or retracted. As shown, rails (228, 230) are slidably disposed within a channel (190) of the housing of handle assembly (112). Channel (190) includes first and second opposing surfaces (192, 194) that limit the movement of first and second rails (228, 230) within channel (190).

FIGS. 10B and 10C show where either distal pawl (216) or proximal pawl (218) is engaged with groove (186) of proximal portion (162). FIG. 10B shows first slider (114) being advanced distally, where proximal pawl (218) of first slider (114) is engaged with groove (186) of dilation catheter (120). More specifically, proximal lateral surface (226) of proximal pawl (218) of first slider (114) is engaged with groove (186) of dilation catheter (120).

As previously described with reference to FIG. 9, rails (228, 230) are coupled together via pin (248). Body (210) of first slider (114) is rotatably positioned on pin (248), such that body (210) may pivotably rock about longitudinal axis of pin (248). As shown in FIG. 9, the longitudinal axis of pin (248) is transverse to longitudinal axis (LA1) of dilation catheter (120). This pivoting about pin (248) connecting first and second rails (228, 230) allows body (210) of first slider (114) to rotate relative to first and second rails (228, 230). As shown, first and second rails (228, 230) slide along longitudinally channel (190) without pivoting. Additionally, using the orientation of FIGS. 10A-10C, first and second rails (228, 230) maintain a horizontal orientation even when body (210) of first slider (114) is pivoted clockwise (shown in FIG. 10B) or counterclockwise (shown in FIG. 10C). When body (210) of first slider (114) is in a pivoted state, first and second springs (240, 242) bend laterally.

As shown in FIG. 10B, first and second springs (240, 242) may compress or otherwise deform when first slider (114) is moved distally along dilation catheter (120). The resilient bias of first and second springs (240, 242) is shown as generally transverse to longitudinal axis (LA1) of dilation catheter (120). In other words, the resilient bias of first and second springs (240, 242) is along a path that is transverse to the longitudinal axis of the spring. As shown, the resilient bias is not along the longitudinal axis of first and second springs (240, 242). The resilient bias is caused by first and second springs (240, 242) wanting to return from the bent state (shown in FIGS. 10B-10C) to the neutral state (shown in FIG. 10A).

FIG. 10C shows first slider (114) being retracted proximally, where distal pawl (216) of first slider (114) is engaged with the corresponding grooves of dilation catheter (120). More specifically, distal lateral surface (222) of distal pawl (216) of first slider (114) is engaged with groove (186) of dilation catheter (120). In FIG. 10C, first and second springs (240, 242) are configured to stretch when first slider (114) is moved proximally along dilation catheter (120).

Teeth (222a, 226a) may be configured to selectively engage grooves (186) of proximal portion (162) of dilation catheter (120). Similar to FIG. 10A, teeth (222a, 226a) of first slider (114) are not configured to engage grooves (186) of dilation catheter (120) when first slider (114) is not being moved distally or proximally along dilation catheter (120). Similar to FIG. 10B, teeth (226a) of proximal pawl (218) are configured to engage grooves (186) when first slider (114) is moved distally. Similar to FIG. 10C, teeth (222a) of distal pawl (216) are configured to engage groove (186) when first slider (114) is moved proximally along exterior (184) of dilation catheter (120).

D. Instrument in a Bent Configuration

FIG. 11 shows the instrument of FIG. 6A with a distal portion of rail (118) in a bent configuration. Each anatomical passageway may require an entry angle that is uniquely associated with that particular anatomical passageway. For instance, entry of a pointing instrument into a maxillary sinus ostium may require an angle of entry that differs from the angle of entry required for entry of a pointing instrument into a frontal recess of a frontal sinus. It may therefore be desirable to provide a pointing instrument with a malleable feature, thereby enabling the operator to adjust the pointing instrument based on the particular passageway that is to be explored. Malleability of rail (118) may also allow the operator to explore different passageways at different entry angles within the same medical procedure, such that the operator may bend the guide feature between explorations to achieve different orientation angles.

As shown, rail (118) is hollow and at least a distal portion of rail (118) is malleable. Rail (118) may be formed entirely of a malleable material (e.g., steel, etc.). Alternatively, it is also envisioned that only a distal portion of rail is malleable while a proximal portion of rail (118) is rigid or otherwise non-malleable. As shown in FIG. 11, at least a distal portion of rail (118) is bendable laterally to position distal end (160) of rail (118) laterally away from the central longitudinal axis of the proximal portion of rail (118). The malleability of rail (118) maintains this bend angle as distal end (160) is advanced through anatomical passageways in head (H) of patient (P). The operator may readily bend rail (118) on an ad hoc basis, before insertion into head (H) of patient (P), with a bend angle that is selected based on the targeted anatomical passageway. In some instances, a separate bending instrument may be used to bend rail (118) to consistently achieve predetermined bend angles. Additionally, a distal portion of rail (118) being malleable allows operator to use instrument (110) as a frontal/maxillary pointer and a frontal/maxillary balloon sinuplasty device. For example, as described previously with respect to FIGS. 6A-7D, dilation catheter (120) may slide over rail (118), such that expandable balloon (136) may be inflated using fluid source (134) in a bent configuration as well as the straight configuration shown and described above with respect to FIGS. 6D and 7D.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An instrument, comprising: (a) a handle assembly; (b) a shaft extending distally from the handle assembly, wherein the shaft includes a distal end that is configured to be introduced into an anatomical passageway within a head of a human; (c) a dilation catheter that includes an expandable dilator, wherein the dilation catheter is configured to advance distally relative to the shaft; and (d) a position sensor configured to generate signals indicating a position of the position sensor within the head of the human, wherein the position sensor is configured to advance distally between at least first and second positions, wherein the position sensor is disposed adjacent the distal end of the shaft in the first position, wherein the position sensor is configured to be carried further distally by the dilation catheter to the second position, wherein in the second position the position sensor is separated a distance from the distal end of the shaft.

EXAMPLE 2

The instrument of Example 1, wherein in the first position a distal end of the dilation catheter is configured to be positioned proximal to the distal end of the shaft.

EXAMPLE 3

The instrument of Example 2, wherein in the second position the distal end of the dilation catheter is configured to be positioned distal to the distal end of the shaft.

EXAMPLE 4

The instrument of any one or more of Examples 1 through 3, wherein in the first position the position sensor is carried by the distal end of the shaft, wherein in the second position the position sensor is carried by a distal end of the dilation catheter.

EXAMPLE 5

The instrument of any one or more of Examples 1 through 4, wherein the position sensor is operatively coupled with a disc having a larger diameter than the shaft such that when the dilation catheter is advanced distally around an exterior surface of the shaft, the dilation catheter carries the position sensor distally.

EXAMPLE 6

The instrument of Example 5, further comprising a light source coupled with the disc.

EXAMPLE 7

The instrument of Example 6, wherein the light source includes an internal battery positioned distally of the expandable dilator.

EXAMPLE 8

The instrument of any one or more of Examples 6 through 7, wherein the disc includes proximal and distal surfaces, wherein the distal surface of the disc is in contact with the light source and the proximal surface of the disc is in contact with the position sensor.

EXAMPLE 9

The instrument of any one or more of Examples 1 through 8, wherein the handle assembly includes first and second advancement mechanisms that are configured to independently advance the dilation catheter distally, wherein the first advancement mechanism is operable to advance the dilation catheter distally a first distance and the second advancement mechanism is operable to advance the dilation catheter distally a second distance.

EXAMPLE 10

The instrument of Example 9, wherein the dilation catheter is configured to not be fully distally advanced until both of the first and second advancement mechanisms are fully advanced on the handle assembly.

EXAMPLE 11

The instrument of any one or more of Examples 9 through 10, wherein the handle assembly includes first and second longitudinally extending channels, wherein the first and second advancement mechanisms include first and second sliders that are configured to slide within the first and second longitudinally extending channels.

EXAMPLE 12

The instrument of Example 11, wherein the first and second longitudinally extending channels are angularly offset by about 90 degrees.

EXAMPLE 13

The instrument of any one or more of Examples 9 through 12, wherein the first and second advancement mechanisms each include a plurality of teeth, wherein an exterior of the dilation catheter includes a plurality of teeth configured to engage the plurality of teeth of the first and second advancement mechanisms only when the first or second advancement mechanisms are being moved distally or proximally along the exterior of the dilation catheter.

EXAMPLE 14

The instrument of Example 13, wherein the plurality of teeth of the first and second advancement mechanisms are configured to not engage the plurality of teeth of the dilation catheter when the first and second advancement mechanisms are not being moved distally or proximally along the dilation catheter.

EXAMPLE 15

The instrument of any one or more of Examples 1 through 14, wherein the shaft is hollow and at least a distal portion of the shaft is malleable.

EXAMPLE 16

An instrument comprising: (a) a handle assembly including first and second longitudinally extending channels; (b) first and second advancement mechanisms configured to move within the respective first and second longitudinally extending channels of the handle assembly; (c) a shaft extending distally from the handle assembly, wherein the shaft includes a distal end that is configured to be introduced into an anatomical passageway within a head of a human; and (d) a dilation catheter including an expandable dilator, wherein each of the first and second advancement mechanisms are operable to only advance the dilation catheter partially.

EXAMPLE 17

The instrument of Example 16, wherein the first and second advancement mechanisms each include a plurality of teeth, wherein an exterior of the dilation catheter includes a plurality of teeth configured to engage the plurality of teeth of the first and second advancement mechanisms only when the first or second advancement mechanisms are being moved distally or proximally along the exterior of the dilation catheter.

EXAMPLE 18

The instrument of any one or more of Examples 16 through 17, wherein the plurality of teeth of the first and second advancement mechanisms are configured to not engage the plurality of teeth of the dilation catheter when the first and second advancement mechanisms are not being moved distally or proximally along the dilation catheter.

EXAMPLE 19

The instrument of any one or more of Examples 16 through 18, wherein the first advancement mechanism includes first and second oppositely disposed rails, wherein the first advancement mechanism includes first and second springs disposed at least partially within cavities of the first and second oppositely disposed rails, wherein the first and second springs are configured to deform when the first advancement mechanism is moved distally along the dilation catheter, wherein the first and second springs are configured to deform when the first advancement mechanism is moved proximally along the dilation catheter, wherein the first and second springs are configured to resiliently urge the first advancement mechanism to disengage the exterior of the dilation catheter.

EXAMPLE 20

A method comprising: (a) inserting a shaft into one or more anatomical passageways in a head of a human, wherein a distal end of the shaft carries a position sensor to a first position; (b) advancing a dilation catheter distally relative to the shaft such that the dilation catheter contacts the position sensor, wherein the dilation catheter includes an expandable dilator; (c) carrying the position sensor further distally to a second position using the dilation catheter, wherein in the second position the position sensor is separated a distance from the distal end of the shaft; and (d) viewing a display on an image guided surgery system, wherein the image guided surgery system displays the position of the position sensor in the head of the human in real time, based on signals from the position sensor.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An instrument, comprising:
   (a) a handle assembly that includes first and second advancement mechanisms that are configured to independently advance the dilation catheter distally, wherein the first advancement mechanism is operable to advance the dilation catheter distally a first distance and the second advancement mechanism is operable to advance the dilation catheter distally a second distance;

(b) a shaft extending distally from the handle assembly, wherein the shaft includes a distal end that is configured to be introduced into an anatomical passageway within a head of a human;

(c) a dilation catheter that includes an expandable dilator, wherein the dilation catheter is configured to advance distally relative to the shaft; and (d) a position sensor configured to be operatively connected with an image guided surgery navigation system and generate signals indicating a position of the position sensor within the head of the human, wherein the position sensor is configured to advance distally between at least first and second positions, wherein the position sensor is disposed adjacent the distal end of the shaft in the first position, wherein the position sensor is configured to be carried further distally by the dilation catheter to the second position, wherein in the second position the position sensor is separated a distance from the distal end of the shaft.

2. The instrument of claim 1, wherein in the first position a distal end of the dilation catheter is configured to be positioned proximal to the distal end of the shaft.

3. The instrument of claim 2, wherein in the second position the distal end of the dilation catheter is configured to be positioned distal to the distal end of the shaft.

4. The instrument of claim 1, wherein in the first position the position sensor is carried by the distal end of the shaft, wherein in the second position the position sensor is carried by a distal end of the dilation catheter.

5. The instrument of claim 1, wherein the position sensor is operatively coupled with a disc having a larger diameter than the shaft such that when the dilation catheter is advanced distally around an exterior surface of the shaft, the dilation catheter carries the position sensor distally.

6. The instrument of claim 5, further comprising a light source coupled with the disc.

7. The instrument of claim 6, wherein the disc includes proximal and distal surfaces, wherein the distal surface of the disc is in contact with the light source and the proximal surface of the disc is in contact with the position sensor.

8. The instrument of claim 1, wherein the dilation catheter is configured to not be fully distally advanced until both of the first and second advancement mechanisms are fully advanced on the handle assembly.

9. The instrument of claim 1, wherein the handle assembly includes first and second longitudinally extending channels, wherein the first and second advancement mechanisms include first and second sliders that are configured to slide within the first and second longitudinally extending channels.

10. The instrument of claim 9, wherein the first and second longitudinally extending channels are angularly offset by about 90 degrees.

11. The instrument of claim 1, wherein the first and second advancement mechanisms each include a plurality of teeth, wherein an exterior of the dilation catheter includes a plurality of teeth configured to engage the plurality of teeth of the first and second advancement mechanisms only when the first or second advancement mechanisms are being moved distally or proximally along the exterior of the dilation catheter.

12. The instrument of claim 11, wherein the plurality of teeth of the first and second advancement mechanisms are configured to not engage the plurality of teeth of the dilation catheter when the first and second advancement mechanisms are not being moved distally or proximally along the dilation catheter.

13. An instrument comprising:

(a) a handle assembly including first and second longitudinally extending channels;

(b) first and second advancement mechanisms configured to move within the respective first and second longitudinally extending channels of the handle assembly;

(c) a shaft extending distally from the handle assembly, wherein the shaft includes a distal end that is configured to be introduced into an anatomical passageway within a head of a human; and (d) a dilation catheter including an expandable dilator, wherein each of the first and second advancement mechanisms are operable to only advance the dilation catheter partially.

14. The instrument of claim 13, wherein the first and second advancement mechanisms each include a plurality of teeth, wherein an exterior of the dilation catheter includes a plurality of teeth configured to engage the plurality of teeth of the first and second advancement mechanisms only when the first or second advancement mechanisms are being moved distally or proximally along the exterior of the dilation catheter.

15. The instrument of claim 14, wherein the plurality of teeth of the first and second advancement mechanisms are configured to not engage the plurality of teeth of the dilation catheter when the first and second advancement mechanisms are not being moved distally or proximally along the dilation catheter.

16. The instrument of claim 13, wherein the first advancement mechanism includes first and second oppositely disposed rails, wherein the first advancement mechanism includes first and second springs disposed at least partially within cavities of the first and second oppositely disposed rails, wherein the first and second springs are configured to deform when the first advancement mechanism is moved distally along the dilation catheter, wherein the first and second springs are configured to deform when the first advancement mechanism is moved proximally along the dilation catheter, wherein the first and second springs are configured to resiliently urge the first advancement mechanism to disengage the exterior of the dilation catheter.

* * * * *